United States Patent [19]
Miller

[11] Patent Number: 5,839,585
[45] Date of Patent: Nov. 24, 1998

[54] METHOD FOR DISPERSING ABSORBENT ARTICLES

[75] Inventor: Carolyn Jeanne Miller, Cincinnati, Ohio

[73] Assignee: The Procter & Gamble Company, Cincinnati, Ohio

[21] Appl. No.: 962,888

[22] Filed: Nov. 7, 1997

Related U.S. Application Data

[63] Continuation of Ser. No. 656,941, May 30, 1996, abandoned.

[51] Int. Cl.$^6$ ........................................................ A47F 7/00
[52] U.S. Cl. ..................... 211/49.1; 211/59.2; 206/45.24; 312/42
[58] Field of Search .................................... 211/49.1, 132, 211/59.2; 248/174; 206/45.24; 312/42

[56] References Cited

U.S. PATENT DOCUMENTS

| | | |
|---|---|---|
| D. 371,707 | 7/1996 | Miles . |
| D. 372,272 | 7/1996 | Frisch . |
| 2,071,040 | 2/1937 | Lloyd . |
| 2,360,573 | 10/1944 | Mena . |
| 3,860,304 | 1/1975 | Bolton . |
| 4,064,880 | 12/1977 | Logan . |
| 4,181,176 | 1/1980 | Frazier . |
| 4,267,726 | 5/1981 | Noik . |
| 4,389,764 | 6/1983 | Flander et al. . |
| 4,429,806 | 2/1984 | Schwarzli . |
| 4,706,845 | 11/1987 | Schnurer et al. . |
| 4,750,640 | 6/1988 | Kobeck et al. . |
| 4,767,022 | 8/1988 | Oldorf . |
| 4,963,072 | 10/1990 | Miley et al. . |
| 5,047,947 | 9/1991 | Stump . |
| 5,167,345 | 12/1992 | Bleeker . |
| 5,178,169 | 1/1993 | Lamle . |
| 5,256,572 | 10/1993 | Tang et al. . |
| 5,467,285 | 11/1995 | Flinn et al. . |
| 5,564,007 | 10/1996 | Kazen-Goudarzi et al. . |
| 5,564,547 | 10/1996 | Ranon et al. . |
| 5,639,235 | 6/1997 | Lapointe et al. . |
| 5,644,693 | 7/1997 | Fitzgerald et al. . |
| 5,691,919 | 11/1997 | Gemmell et al. . |

FOREIGN PATENT DOCUMENTS

| | | |
|---|---|---|
| 1 356 956 | 2/1964 | France . |
| 805 066 | 5/1951 | Germany . |
| 3144944 A1 | 5/1983 | Germany . |
| 3641614 A1 | 6/1988 | Germany . |
| 130379 | 12/1928 | Switzerland . |
| 2 271 559 | 4/1994 | United Kingdom . |

OTHER PUBLICATIONS

Side panel of Stayfree Surefit sanitary napkin, manufactured by McNeil–PPC, New Jersey.

*Primary Examiner*—Robert W. Gibson, Jr.
*Attorney, Agent, or Firm*—Matthew P. Fitzpatrick; Jeffrey V. Bamber; Steven W. Miller

[57] ABSTRACT

A method for dispensing absorbent articles for use by individuals, said method comprising a dispensing device containing at least two different types of absorbent articles and a means for allowing an individual to select one or more types of the absorbent articles in the dispensing device.

12 Claims, 1 Drawing Sheet

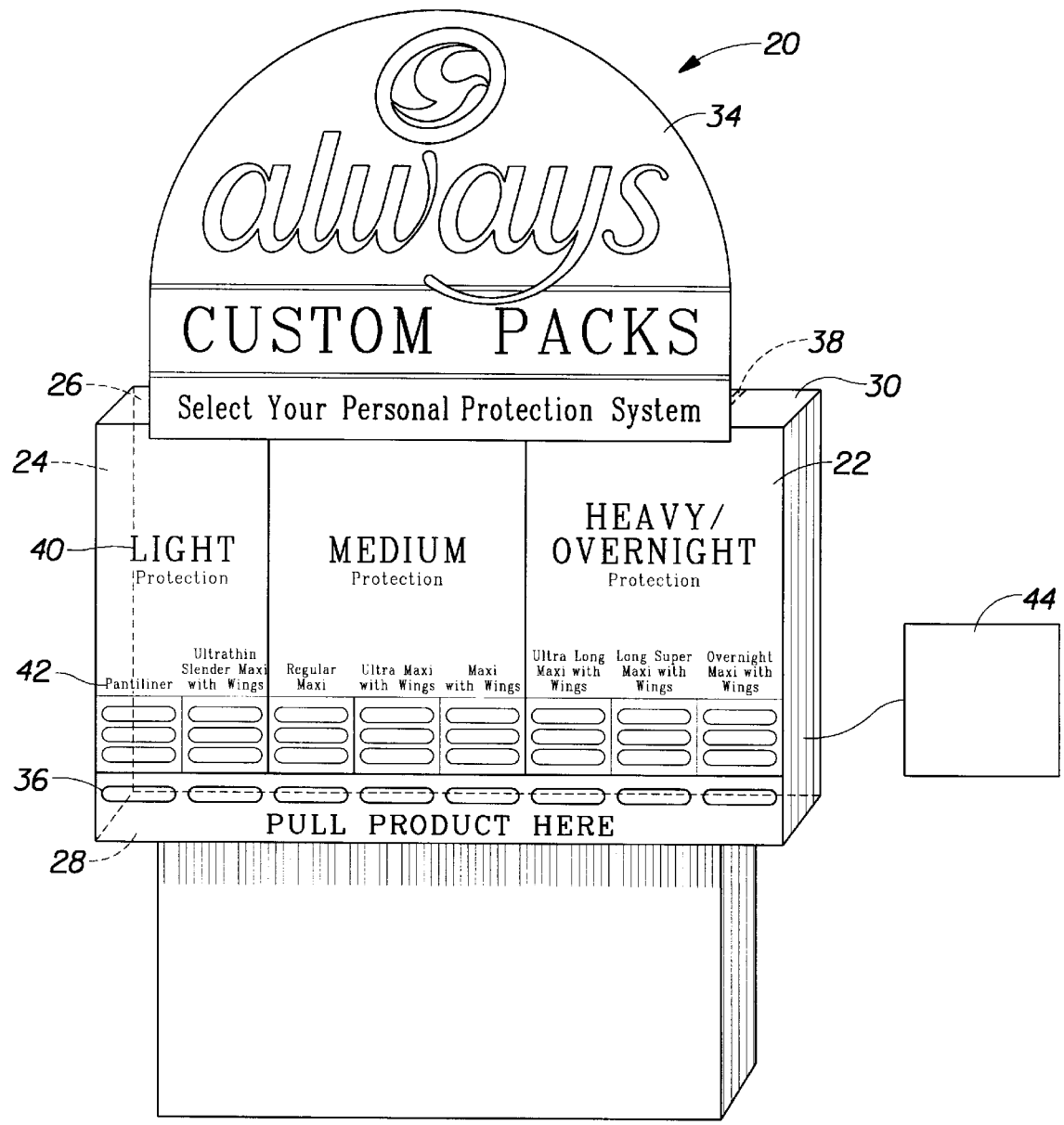

METHOD FOR DISPERSING ABSORBENT ARTICLES

This is a continuation of application Ser. No. 08/659,941, filed on May 30, 1996, now abandoned.

FIELD OF THE INVENTION

This invention relates to a method for dispensing absorbent articles for use by individuals, and more particularly to a method for dispensing absorbent articles that allows individuals to select absorbent articles having different characteristics.

BACKGROUND OF THE INVNTION

Absorbent articles function both to contain discharged materials and to isolate these materials from the body of the wearer and from the wearer's garments and bed clothing. Disposable absorbent articles having many different basic designs are known to the art . However, there are some key features of absorbent articles, particularly catamenial products, that effect the performance of such products.

For example, the absorbent capacity of an absorbent article necessary to provide containment of bodily fluids without leaking is quite different between daytime and overnight use. Because wear time is usually longer during overnight use as compared to daytime use, the quantity of bodily fluids discharged during overnight use is typically greater than the quantity of bodily fluids discharged during daytime use. Even though the absorbent capacity requirements are quite different, absorbent articles having one level of absorbent capacity are typically used for both daytime and overnight use. Unfortunately, the absorbent capacity is sometimes insufficient for overnight use and the absorbent article leaks.

It has been found in developing the present invention, that providing consumers, particularly those who use catamenial products, with a combination of systems of different product types (different thicknesses, lengths, types of product features (e.g., wings/non-wings)) provides the consumer with superior protection and comfort versus a single type of product for all uses.

Currently, absorbent articles such as catamenial products are typically sold in packages containing quantities of ten to twenty products. Such packages currently sell for around three to four dollars in the United States. This may be considerably more than a consumer is willing to spend if she either only needs a small quantity of such a product, or if she wishes to experiment by trying a product that she has never used before. In addition, these packages can be fairly bulky and take up a relatively large space in a consumer's shelves or closets, should the consumer have more than one type of product in her home. There is currently no means for individuals to select individual products, or small quantities of products for purchase, or to assemble products to form a system of protection.

In addition, the number of different types of catamenial products often makes it confusing to feminine hygiene consumers which products would best meet their protection needs. In a recent survey, roughly 70% of consumers reported purchasing the wrong type of sanitary napkin and/or pantiliner within the six month period preceding the survey.

Therefore, it is an object of the present invention to provide a method for dispensing absorbent articles that allows individuals to properly select among various absorbent articles having different characteristics.

It is another object of the present invention to provide a method for dispensing absorbent articles that allows individuals to select a combination of absorbent articles having different characteristics to form a system of protection.

It is also an object of the present invention to produce a method for dispensing absorbent articles, particularly catamenial products, that allows consumers to economically try a variety of different types of absorbent articles.

These and other objects of the present invention will be more readily apparent when considered in reference to the following description and when taken in conjunction with the accompanying FIGURE.

SUMMARY OF THE INVENTION

The present invention provides a method for dispensing absorbent articles for use by individuals, especially catamenial products. More particularly, this invention relates to a method for dispensing absorbent articles that allows individuals to select absorbent articles having different characteristics. The method comprises a dispensing device containing at least two different types of absorbent articles and a means for allowing an individual to select one or more types of the absorbent articles in the dispensing device. At least one of the types of absorbent articles in the dispensing device is available in quantities of less than the quantities currently sold commercially. The method of the present invention preferably further comprises a mechanism for conveying to a consumer a description of a suitable system of catamenial protection. This mechanism can be an interactive computer that prompts a consumer to input several (e.g., three to four) key pieces of information about their menstrual cycle, and based upon this, provide the consumer with a recommendation or prescription of a system of products that will optimize the use of the products in the dispensing device.

BRIEF DESCRIPTION OF THE DRAWINGS

While the specification concludes with claims particularly pointing out and distinctly claiming the subject matter which is regarded as forming the present invention, it is believed that the present invention will be better understood from the following description which is taken in conjunction with the accompanying drawings in which like designations are used to designate substantially identical elements and in which:

The FIGURE is a perspective view of one embodiment of a dispensing device used in the method of the present invention.

DETAILED DESCRIPTION OF THE INVENTION

The method of the present invention relates to a dispensing device containing at least two different types of absorbent articles and a means for allowing an individual to select one or more types of the absorbent articles in the dispensing device.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably to be recycled, composted or otherwise disposed of in an environmentally compatible manner). The term "absorbent articles" includes sanitary napkins, panty liners (or pantiliners), incontinence devices, interlabial products, tampons, diapers, and training pants.

In the preferred embodiment shown in the FIGURE the dispensing device comprises a stand alone display for use in a retail establishment, such as a grocery store. In the embodiment shown in the FIGURE the dispensing device 20 dispenses different types of catamenial devices. The term "catamenial devices", as used herein includes, but is not limited to sanitary napkins, pantiliners, incontinence devices, interlabial products, and tampons.

The dispensing device 20 can be in any suitable configuration. The dispensing device 20 shown in the FIGURE comprises a front panel 22, a pair of side panels 24, a rear panel 26, a bottom 28, a top 30, a base 32, a display sign 34, and a discharge portion 36. The dispensing device 20 shown in FIGURE preferably also comprises at least one partition 38, and more preferably, a plurality of partitions, in its interior for segregating different types of products. A plurality of products of each type are preferably vertically stacked between partitions 38. The discharge portion preferably comprises a plurality of openings or discharge ports 36. The catamenial devices are preferably fed by gravity into the discharge ports 36 when a catamenial product is removed from the bottom of the stack. The dispensing device 20 can be made of any suitable material, including metal, wood, plastic, and cardboard.

The dispensing device can contain any number of different types of catamenial products. Typically, the dispensing device 20 will contain between 2 and 15, or more, different types of catamenial products. In the preferred embodiment shown in the FIGURE the dispensing device 20 contains eight different types of catamenial products. The dispensing device 20 can be labeled with a first level of indicia, or first indicia 40, to assist the user or consumer in determining which types of catamenial devices are best suited to her needs. For example, suitable first indicia 40 could be (from left to right) "LIGHT Protection", "MEDIUM Protection", and "HEAVY/OVERNIGHT Protection".

The dispensing device 20 can be further provided with a second level of indicia or second indicia 42, to indicate the product selection. Suitable second indicia 42 can comprise (from left to right), under the category of "LIGHT Protection", "Pantiliner" and "Ultrathin Slender Maxi with Wings". Suitable indicia under the category of "MEDIUM Protection" can comprise (from left to right) "Regular Maxi", "Ultra Maxi with Wings" and "Maxi with Wings". Suitable indicia under the category of "HEAVY/ OVERNIGHT Protection" can comprise (from left to right) "Ultra Long Maxi with Wings", "Long Super Maxi with Wings", and "Overnight Maxi with Wings".

The products within the dispensing device 20 allow the consumer to select from a combination of different absorbencies, product thicknesses, lengths, types of product features (wings/non-wings) to provide consumers with a range of light/medium/and heavy protection. The individual products dispensed for each category of product labeled with the second indicia 42 can comprise, by way of example, the following commercially available catamenial products manufactured by The Procter & Gamble Company of Cincinnati, Ohio: ALWAYS® Pantiliner with DriWeave® manufactured under U.S. Pat. Nos. 4,324,246 and 4,463, 045; ALWAYS® Ultrathin Slender Maxi with Wings manufactured under U.S. Pat. Nos. 4,342,314, 4,463,045, 4,556, 146, B1 4,589,876, 4,687,478, 4,950,264, 5,009,653, 5,267, 992, and Re. 32,649; ALWAYS® Regular Maxi; ALWAYS® Ultra Maxi with Wings; ALWAYS ® Maxi with Wings; ALWAYS® Ultra Long Maxi with Wings; ALWAYS® Long Super Maxi with Wings; and ALWAYS® Overnight Maxi with Wings.

The individual products are preferably dispensed in packages containing quantities ranging from 1–10 products per package, and preferably between 2–9 products per package. It should also be noted that if one type of product is dispensed in a quantity of 10, then at least one different type of product is preferably dispensed in a quantity of less than 10. The packages containing such quantities of products are preferably some suitable, preferably flat (for stacking) plastic bag. Preferably, the individual products are dispensed in a 5-count package for the ALWAYS® Pantiliners with DRIWEAVE® products, and in 4-count packages for the ALWAYS® Ultrathin Slender Maxi with Wings and the catamenial products in the "MEDIUM Protection" category. The products in the "HEAVY/OVERNIGHT Protection" category are preferably packaged in 3-count packages due to their larger size. The individual products inside the plastic bag may also be provided in their own individual wrapper, such as is described in U.S. Pat. No. 4,556,146.

To use the dispensing device 20, the consumer will pull the desired product package, or combinations of different products or product packages from the discharge portion 36 of the dispensing device. If the product is not the proper product for the consumers needs, the consumer can put the product package back in the product storage bin at the top of the dispensing device 20 (if the dispensing device 20 is provided with an open top). After making the correct selection, the consumer can then pay for the packages of products at the check out counter at the front of the store.

The method of the present invention allows the consumer to more economically try a variety of different types of absorbent products. It also allows the consumer to mix and match small, more affordable quantities of light, medium, and heavy protection to create a personal protection system to meet the consumer's individual needs. The dispensing device provides an easy to understand explanation of the different absorbent articles that can be selected as part of an individual's protection system.

Various alternative embodiments of the method of the present invention are possible. While the present invention is particularly suitable for providing consumers with a means for selecting an individual catamenial protection system, in other embodiments, the dispensing device 20 could include other types of absorbent articles, such as incontinence devices, diapers, and training pants.

In other alternative embodiments, the dispensing device 20 can be provided with a mechanism 44 or means for conveying to a consumer a description of a suitable system of protection, such as a system of catamenial protection. Suitable mechanisms for conveying this information to a consumer can include, but are not limited to a chart that the consumer can read, a dial that the consumer can move to identify her needs and obtain an indication of a suitable system of protection, or an interactive computer. The latter type device (the interactive computer) can, for instance, prompt a consumer to input several (e.g., three to four) key pieces of information about their menstrual cycle, body type and size, current product type preference, and based upon this, provide the consumer with a recommendation or prescription of a system of products that will optimize the use of the products in the dispensing device 20. Such key pieces of information can include perceived flow (e.g., light, moderate, or heavy), panty size (e.g., from 5 to 10), current preferred product thickness and product length.

In still other embodiments, more automated types of product selection and dispensing systems currently available could be used. In yet other embodiments, the product dispensing device 20 of the present invention could group together and package or wrap the products selected for the individual protection system into a single package for the consumer. Such a dispensing device could be combined with one of the mechanisms 44 described above.

The disclosures of all patents, as well as any corresponding published foreign patent applications), and publications mentioned throughout this patent application are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for dispensing absorbent articles of different types for use by individuals, said method comprising the steps of:
    a) providing a supply of at least two different types of absorbent articles, said absorbent articles being packaged in packages containing between 2 and 9 absorbent articles per package, inclusive;
    b) providing a dispensing device, said supply of at least two different types of absorbent articles being housed within said dispensing device; and
    c) providing said dispensing device with means for allowing an individual to select one or more types of absorbent articles housed within said dispensing device.

2. The method of claim 1 wherein said dispensing device is a stand alone display.

3. The method of claim 1 wherein said absorbent articles within said packages are also individually packaged.

4. The method of claim 1 wherein said absorbent articles comprise catamenial devices.

5. The method of claim 1 wherein at least some of said absorbent articles comprise incontinence devices, diapers, or training pants.

6. An interactive method for dispensing absorbent articles of different types for use by individuals, said interactive method comprising the steps of:
    a) providing a supply of at least two different types of absorbent articles,
    b) providing a dispensing device for dispensing said supply of absorbent articles, said supply of at least two different types of absorbent articles being housed within said dispensing device,
    c) conveying information to a consumer describing a suitable system of catamenial protection, said system comprising at least two different types of absorbent articles, and
    d) providing said dispensing device with means for allowing a consumer to select two or more types of absorbent articles from said supply of absorbent articles housed within said dispensing device.

7. The method of claim 6 wherein said supply of absorbent articles is packaged in packages containing quantities of between 2 and 9 absorbent articles per package, inclusive.

8. The method of claim 7 wherein said absorbent articles within said packages are also individually packaged.

9. The method of claim 6 wherein said dispensing device is a stand alone display.

10. The method of claim 6 wherein said step of conveying information to a consumer describing a suitable system of catamenial protection is accomplished through the use of an interactive computer.

11. The method of claim 6 further comprising the step of:
    e) providing said dispensing device with a supply of packages so that as a consumer removes said selected absorbent articles from said dispensing device, said absorbent articles may be placed in one or more of said packages.

12. A method of providing a system for the use of feminine hygiene products to a consumer, said method comprising the steps of:
    a) collecting information from a consumer regarding her body size and menstrual cycle characteristics;
    b) selecting a system of feminine hygiene products from at least two available systems, wherein each of said available systems is comprised of at least two different feminine hygiene products, and wherein said selected system of feminine hygiene products is selected based upon said information collected from said consumer;
    c) providing information to said consumer identifying the feminine hygiene products which make up said selected system;
    d) providing a dispensing device containing the feminine hygiene products which comprise said at least two available systems; and
    e) providing said dispensing device with means for allowing said consumer to retrieve and use the feminine hygiene products which make up said selected system.

* * * * *